(12) United States Patent
Miller et al.

(10) Patent No.: US 7,014,816 B2
(45) Date of Patent: Mar. 21, 2006

(54) FOOD QUALITY INDICATOR DEVICE

(75) Inventors: Dwight W. Miller, Pine Bluff, AR (US); Jon G. Wilkes, Little Rock, AR (US); Eric D. Conte, Bowling Green, KY (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 391 days.

(21) Appl. No.: 10/005,004

(22) Filed: Dec. 4, 2001

(65) Prior Publication Data

US 2002/0044891 A1 Apr. 18, 2002

Related U.S. Application Data

(63) Continuation of application No. 09/116,152, filed on Jul. 16, 1998, now abandoned.
(60) Provisional application No. 60/052,674, filed on Jul. 16, 1997.

(51) Int. Cl.
*G01N 31/22* (2006.01)
*G01N 21/17* (2006.01)
*G01N 33/02* (2006.01)

(52) U.S. Cl. .......................... 422/87; 422/56; 422/57; 422/58; 422/86; 436/20; 436/21; 436/111; 436/169

(58) Field of Classification Search ............ 422/56–58, 422/86–87; 436/20–21, 111, 113, 169
See application file for complete search history.

(56) References Cited

U.S. PATENT DOCUMENTS

| | | | |
|---|---|---|---|
| 2,626,855 A | 1/1953 | Hand | |
| 3,025,142 A | 3/1962 | Williams | |
| 3,681,027 A | 8/1972 | Smith | |
| 3,751,382 A | * 8/1973 | Ljungberg et al. | 435/12 |
| 3,992,153 A | 11/1976 | Ferber et al. | |
| 4,063,452 A | 12/1977 | Bradshaw | |
| 4,195,055 A | * 3/1980 | Patel | 422/56 |
| 4,268,478 A | 5/1981 | Huber | |
| 4,301,027 A | * 11/1981 | Blumcke et al. | 436/183 |
| 4,309,185 A | 1/1982 | Simon et al. | |
| 4,327,575 A | 5/1982 | Locker | |
| 4,348,358 A | 9/1982 | McKee et al. | |
| 4,432,656 A | * 2/1984 | Allmendinger | 374/102 |
| 4,459,266 A | 7/1984 | Lamoreaux | |
| 4,485,665 A | 12/1984 | Norman | |
| 4,495,291 A | 1/1985 | Lawton | |
| 4,746,616 A | 5/1988 | Honigs et al. | |
| 4,752,447 A | 6/1988 | Kimmel et al. | |
| 4,840,919 A | 6/1989 | Attar | |
| 4,980,294 A | 12/1990 | Elias et al. | |
| 5,045,283 A | 9/1991 | Patel | |
| 5,053,339 A | 10/1991 | Patel | |
| 5,183,763 A | 2/1993 | Mallow et al. | |
| 5,407,829 A | 4/1995 | Wolfbeis et al. | |
| 5,439,648 A | 8/1995 | Balderson et al. | |
| 5,501,836 A | 3/1996 | Myerson | |
| 5,501,945 A | 3/1996 | Kanakkanatt | |
| 5,599,913 A | 2/1997 | Harris et al. | |
| 5,753,285 A | 5/1998 | Horan | |

FOREIGN PATENT DOCUMENTS

| | | |
|---|---|---|
| DE | 195 22 610 C1 | 12/1996 |
| EP | 0 193 036 A2 | 9/1986 |
| EP | 0 449 798 A2 | 10/1991 |
| WO | WO 93/15403 | 8/1993 |

* cited by examiner

Primary Examiner—A Soderquist
(74) Attorney, Agent, or Firm—Merchant & Gould P.C.

(57) ABSTRACT

A food quality indicator device an indicator compound provided on a substrate. The indicator compound changes color due to the presence of volatile compounds, such as volatile bases, in spoiled food, even when the food is frozen. Alternatively, the indicator compound detects the presence of an unwanted amine-producing biological agent, such as bacteria or fungi. The indicator compound is typically contained within a polymeric matrix disposed on the substrate. Examples of suitable indicator compounds include halogenated azo dyes, sulfonated xanthene dyes, and sulfonated hydroxy-functional triphenylmethane dyes.

15 Claims, 2 Drawing Sheets

FOOD QUALITY INDICATOR DEVICE

The present application is a continuation of application Ser. No. 09/116,152, filed 16 Jul. 1998, now abandoned, which application(s) are incorporated herein by reference.

The present application is related to U.S. provisional application Ser. No. 60/052,674 filed on Jul. 16, 1997, entitled "Food Quality Indicator Device", the contents of which are incorporated herein by reference.

FIELD OF THE INVENTION

The present invention is directed generally to a device for indicating the quality of food. In particular, the present invention is directed to a device having an indicator compound disposed on a substrate for colorimetrically indicating the quality of food, including frozen food.

BACKGROUND

The determination of whether food has spoiled is of interest to a large number of people ranging from the food producer to the consumer, including grocers, regulators, importers, exporters, and brokers. Many food products can spoil, including grains, fruits, and vegetables. However, one of the greatest areas of concern is spoilage of red meat, pork, poultry, processed meat products, and seafood. Spoiled foods pose many risks, chief among which is illness caused by consuming the food. Such illnesses may be life-threatening, especially for very young or very old consumers, as well as persons with compromised immune systems.

Many foods are now packaged and/or frozen to retard spoilage. Unfortunately, packaged and frozen foods, which account for a large number of the available red meat, pork, poultry, processed meat, and seafood products, are harder to test for spoilage. Packaged food often needs to be unwrapped, examined, and then repackaged if acceptable. Frozen food typically needs to be thawed in order to determine the quality of the food by current techniques, which often rely on color, smell, and texture. One method still used by the United States Food and Drug Administration for the testing of seafood is organoleptic analysis. This method requires thawing the seafood followed by an olfactory analysis by highly trained experts to determine the condition of the food.

Devices for ascertaining the quality of frozen food, which do not require thawing the food, do exist. However, such devices are typically bulky and are not readily available and/or easily operated and interpreted by inexperienced individuals, such as consumers and grocers.

There is a need for a simple, quick, and effective device for determining the quality of food products to indicate if they are unsafe due to spoilage. In addition, there is a need for a device that can be packaged with food products which is effective in all typical food storage conditions, including temperatures below 0° C. Such a device should be made of materials that are suitable for use with food products and do not contain or generate harmful chemicals. In addition, the device should provide indications of food quality that are easily read and understood by all or nearly all of the population.

SUMMARY

The present invention is directed to a device that fulfills these needs. One aspect of the present invention is directed to an indicator device having a substrate and an indicator compound provided on the substrate. The indicator compound is colorimetrically responsive to volatile bases generated by food decomposition at temperatures below 0° C. Indicator devices can also be used to detect other volatile compounds, including volatile acids.

Another embodiment of this aspect includes an indicator compound with a color transition within a range from about pH 1.0 to about pH 6.0. A further embodiment includes an indicator compound that is a halogenated xanthene dye, sulphonated azo dye, or a sulphonated hydroxy-functional triphenylmethane dye. Another embodiment includes a polymeric matrix coated on the substrate, within which the indicator compound is held.

Another aspect of the invention is a method of making an indicator device, which includes forming a solution of an indicator compound, a solvent, and an acid. A silane monomer material is added to the solution. The solution is disposed on a substrate and the silane monomer polymerizes to form a silica matrix in which the indicator compound is disposed.

Another aspect is a method of detecting spoilage in frozen food by providing an indicator device having a substrate and an indicator compound on the substrate. The indicator compound is colorimetrically responsive at temperatures below 0° C. to volatile bases generated by spoiled frozen food. The indicator device and the indicator compound are exposed to the food and then the device is visually inspected to determine if the food is spoiled.

A further aspect is a food package for use with a food product. The food package includes packaging for a food product and an indicator device. The indicator device includes substrate and an indicator compound provided on the substrate. The indicator compound is colorimetrically responsive to volatile bases generated by food decomposition at temperatures below 0° C. The indicator device is associated with the packaging so as to be exposed to volatile bases emitted from the food product.

Another aspect is a method for detecting the presence of an unwanted amine-producing biological agent on a food product. An indicator device is exposed to the food product. The indicator device has a substrate and an indicator compound disposed on the substrate. The indicator compound is colorimetrically responsive to volatile bases emitted by the unwanted amine-producing biological agent. The device is visually inspected to determine if the food product contains the unwanted biological agent by observing if the indicator compound has changed color.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
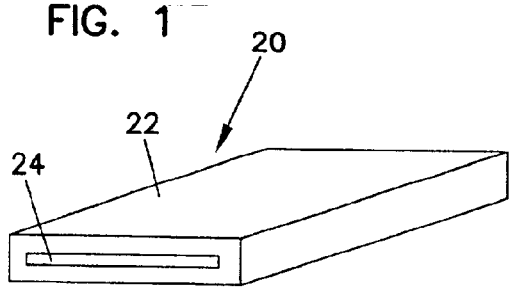
FIG. 1 is a side perspective view of one embodiment of a food quality indicator device according to the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE ILLUSTRATED EMBODIMENTS

The present invention is believed to be applicable to a number of devices and methods for the colorimetric determination of food quality. While the present invention is not so limited, an appreciation of various aspects of the invention will be gained through a discussion of the devices and methods in connection with the detection of spoilage in red meat, pork, poultry, processed meat, and seafood products, and in particular, the detection of spoilage in seafood products, including both freshwater and marine fish and shellfish.

One embodiment of the present invention is illustrated in FIG. 1. A food quality indicator device 20 includes an indicator layer 22 disposed on a substrate 24. Substrate 24 is made from materials capable of supporting indicator layer 22, such as paper, plastic (e.g., polyester, polyethylene, polyvinyl chloride), cotton, flax, resin, glass, fiber glass, or fabric. In some embodiments, indicator layer 22 is formed on the fibers of substrate 24. Substrate 24 may have a variety of shapes and forms. For example, substrate 24 may be a strip, a sheet, or a string. In some embodiments, substrate 24 is part of food packaging material or is adhered to food packaging materials. The thickness of substrate 24 may vary. For substrates that readily absorb the chemicals in indicator layer 22, the thickness of the substrate may be limited in some embodiments to reduce the amount of absorbed chemicals.

Indicator layer 22 typically includes a polymeric matrix and one or more indicator compounds held within the matrix. The indicator compounds are usually dye compounds capable of colorimetrically indicating the presence of one or more chemical compounds associated with the decomposition or spoilage of food. In particular, the indicator compounds are capable of indicating the presence of decomposition products at temperatures below the freezing point of water. In this case, the indicator compounds should be responsive to decomposition compounds in the absence of water mediation.

There are a number of chemical compounds that are generated as food decomposes and spoils. Many foods that contain substantial amounts of protein materials, including red meat, pork, poultry, processed meat, and seafood products, generate volatile compounds, such as volatile bases, during decomposition. Amines comprise one group of volatile bases generated by decomposing food through processes such as the deamination of free amino acids and the degradation of nucleotides. Among the generated amines are ammonia, dimethylamine, and trimethylamine. Dimethylamine and trimethylamine are at least partially volatilized even in frozen food. Other amines associated with decomposing food include histimine, cadaverine, putrescine, indole, spermine, and spermidine. These compounds may also volatilize. These and other compounds comprise the total amount of organic bases formed during the decomposition of food.

In general, the indicator compound in indicator layer 22 changes colors in the presence of these volatile bases. The particular range of concentrations of volatile bases that will cause a color change of the indicator compound depends on factors such as the particular indicator compound used in the device, the chemical environment in which the indicator compound is placed (e.g., the acidity or basicity of the environment), and the amount of indicator that is used in the device. The appropriate range can be determined for each food product by, for example, calibration with test samples. It is expected that different food products will produce different amounts of volatile bases when spoiled. However, food products that are similar (e.g., different types of fish) may generate similar amounts of volatile bases.

The range of concentrations of generated volatile bases that cause a color change in the indicator compound may be chosen to indicate a variety of conditions. For example, the color change may indicate that the food is unsafe for consumption or that the food will soon become unfit for consumption.

In other embodiments, the presence of an unwanted amine-producing biological agent, such as bacteria or fungus, may be detected instead of or in addition to food decomposition. A color change of the indicator compound may indicate the presence of an unwanted biological agent, such as bacteria or fungi. For example, certain fungi generate amines when in contact with grains. In particular, smut on unprocessed wheat stored in silos or in cargo holds of ships generates trimethylamine. Although, the invention is described herein with reference to the detection of food decomposition, it will be appreciated that the same devices, methods, and principles can be applied to the detection of unwanted biological agents.

Indicator compounds for use in the present invention typically have a color change in a range from about pH 1.0 and about pH 6.0, and preferably in a range from about pH 2.5 and pH 5.0, in aqueous solution. Ideal indicators are non-toxic and, preferably, can be used as food additives or dyes, thereby minimizing any danger that might occur if the indicator compound leaks from the food quality indicator device. Preferably, the indicator compounds are approved by a regulatory agency, such as the U.S. Food & Drug Administration, for use with food products. In addition, the ideal indicators have a strong color change upon detection of the volatile bases and the color change is apparent even to color blind members of the population. However, indicators without these particular characteristics may also be used.

Indicators for use in the food quality indicator device should be capable of changing colors at temperatures below the freezing point of water. This means that the color forming chemical reaction of the indicator with the volatile bases emitted by the decomposed food does not rely on mediation by water. Many commercial pH indicator strips state in their instructions that the strip must be placed in contact with an aqueous solution and read while wet. Experiments using these strips, detailed hereinafter, indicate that the strips do not respond appropriately to bases emitted by spoiled frozen fish.

Classes of suitable indicators include xanthene dyes, azo dyes, and hydroxy-functional triphenylmethane dyes. A number of these indicators contain phenol functionalities. Many suitable indicators are halogenated and/or contain acidic functional groups, such as —COOH, —SO$_3$, or —S(O$_2$)O— or salts thereof. Preferred indicators include halogenated xanthene dyes such as Phloxine B, Rose Bengal, or Erythrosine; sulfonated azo dyes such as Congo Red and Metanil Yellow; and sulfonated hydroxy-functional triphenylmethane dyes such as Bromophenol Blue, Bromocresol Green, and Phenol Red. The most preferred indicators for use with frozen seafood are Phloxine B, Rose Bengal, and Bromophenol Blue.

The indicator compound is typically held within a polymeric matrix to prevent leakage of the indicator compound into the food. The polymeric matrix may be adapted to clathrate the indicator compound. Suitable polymeric matrices are at least partially permeable to one or more of the volatile bases to be detected. Preferably, the polymeric matrix is also water-repellent, non-toxic, transparent, and made from reagents suitable, and preferably approved, for use with food or food packaging materials. Examples of such polymeric matrices include matrices made from silicone polymers including polydimethyl silicones, silane titanium oxide sol-gels, silane cross-linkable resins, polyvinylchloride, and butylated cellulose.

One particularly useful polymeric matrix is a sol-gel glass formed by hydrolysis of one or more alkoxysilanes. Suitable alkoxysilanes include tetraalkoxysilanes and alkyl trialkoxysilanes, where the alkyl group is a C1 to C30 straight or branched-chain alkyl group and the alkoxy group is a C1 to C4 alkoxy group. Examples of suitable alkoxysilanes include tetramethoxysilane, tetraethoxysilane, alkyl trimethoxysilane, and alkyl triethoxysilane.

Generally polymerization of the alkoxysilanes may be acid or base catalyzed, typically in the presence of water. Useful catalysts of this polymerization reaction include high-volatility acids such as hydrochloric acid, acetic acid, formic acid, or trifluoroacetic acid.

Indicator layer 22 may also include other additives such as a polymeric resin, hydrated alumina, or a non-volatile acid. The polymeric resin may be added to increase the strength or stiffness of the polymeric layer. One example of a suitable resin is polyvinyl alcohol (PVA) with an average molecular weight of about 5,000 to 20,000.

Hydrated alumina can be added to help retain the volatile bases on the indicator device. This may provide additional stability to the color change observed with the strip, thereby making the color change irreversible or slowly reversing. One example of suitable hydrated alumina compounds with demonstrated use in the present invention is zeolites. Zeolites are well-known for their ability to retain molecules, like ammonia.

Non-volatile acids may be added to control the rate of response or the detection sensitivity of the food quality indicator device. While no particular theory is integral to the invention, it is thought that the acid may alter the acid loading of the polymeric matrix, thereby altering the amount of volatile base that is needed to cause the indicator compound to change color. Suitable acids include concentrated sulfuric acid, sulfamic acid, phosphoric acid, zeolites, alumina, polyacrylic acid, and a sulfonated perfluoroethylene, such as Naphion®-H.

Typically, indicator layer 22 is applied to substrate 24 before or during the polymerization of the polymeric matrix to provide good adhesion of the indicator layer to the substrate. Application of indicator layer 22 to substrate 24 may be accomplished by a variety of techniques including dipping the substrate in the solution, spraying the solution on the substrate, brushing the solution onto the substrate, or pouring the solution over the substrate. In one embodiment, the indicator layer is applied so that the indicator layer forms a letter, number, or symbol that becomes apparent or changes color in the presence of spoiled food. In another embodiment, the substrate or an optional backing material is colored to provide additional contrast for the color change of the indicator compound. For example, the substrate or optional backing material may be white. Alternatively, the substrate or optional backing material may have a color similar to the color of the indicator prior to exposure to spoiled food. The color change of the indicator compound can then be contrasted with the color of an adjacent portion of the substrate or optional backing material that is not covered by the indicator layer.

Figure 2:
FIG. 2 is a side perspective view of another embodiment of a food quality indicator device that includes a shield layer according to the present invention.
Figure 2:
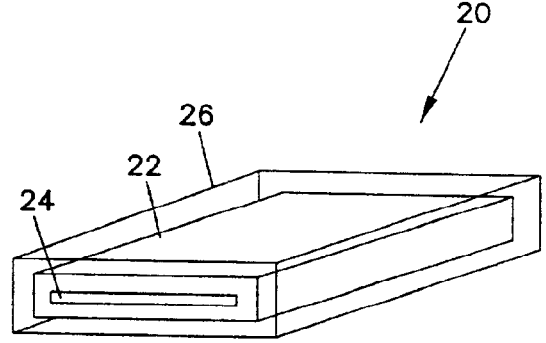

FIG. 2 illustrates another embodiment of the invention in which the indicator layer 22 and substrate 20 are surrounded by a shield layer 26. Shield layer 26 may be attached to indicator layer 22 and/or substrate 24 by a variety of methods including in situ polymerization, heat sealing, ultrasonic welding, or adhesive attachment.

In one embodiment, shield layer 26 is an amine permeable, water repellent polymer that serves to protect the underlying indicator layer from damage and/or further prevents leakage of the indicator compound from the device. This shield layer may be made of the same material as the polymeric matrix of the indicator layer, but other polymers are also acceptable. Suitable polymers for use in this type of shield layer include silica sol-gels, silicone polymers including polydimethyl silicones, silane titanium oxide sol-gels, silane cross-linkable resins, polytetrafluoroethylene (e.g., Teflon™), polyvinylchloride, or butylated cellulose. The shield layer is typically about 10 to 100 $\mu$m thick so that the amount of amine vapor reaching the indicator layer is not reduced below detectable levels.

In another embodiment, shield layer 26 is impermeable to amine vapors. This shield layer may also be water repellent, non-toxic, transparent, and/or made from reagents that are appropriate for use with food packaging. Suitable polymeric materials for this type of shield layer include polypropylene, polyethylene, polystyrene, and copolymers of polystyrene such as ABS (a copolymer made from acrylonitrile, butadiene, and styrene monomers) or poly(styrene-butadiene).

Figure 3A:
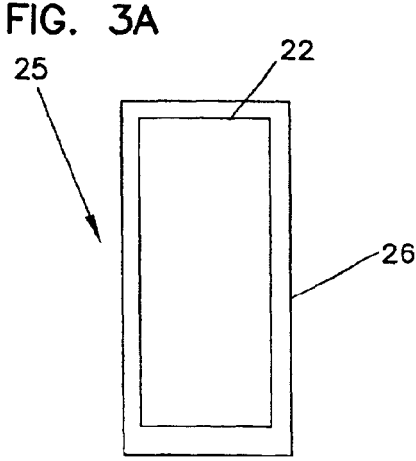
FIGS. 3A–3D are top sectional views of an embodiment of a food quality indicator device according to the present invention, illustrating a method of obtaining quantitative or semiquantitative measurements of the food quality.
Figure 3B:
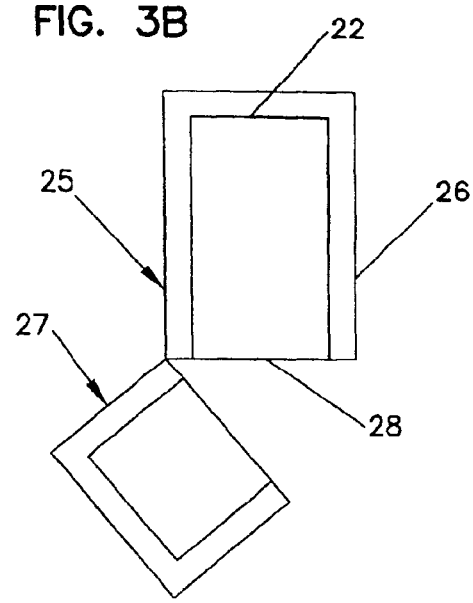
Figure 3C:
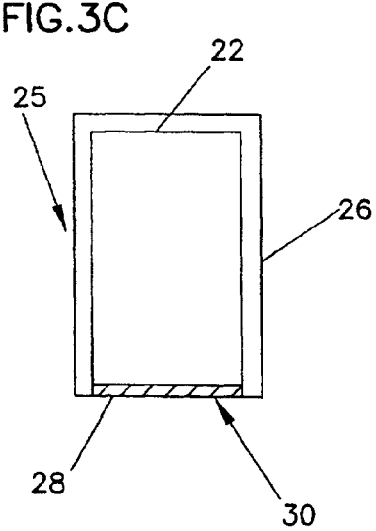
Figure 3D:
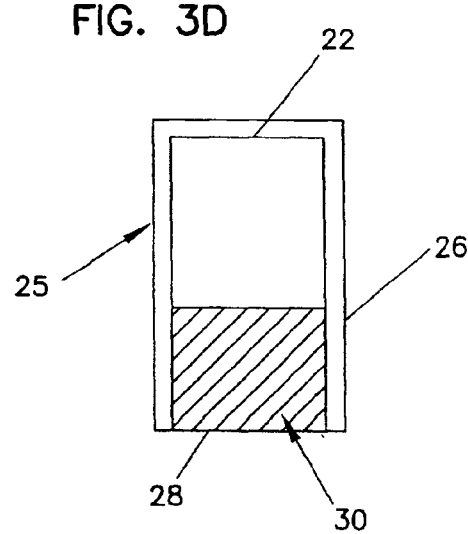

One exemplary embodiment of the invention having the amine-impermeable shield layer is illustrated in FIG. 3A (in which the relative difference in size between the shield layer 26 and indicator layer 22 has been exaggerated for illustrative purposes). The illustrated embodiment is an indicator strip 25 that can be used to provide a quantitative or semiquantitative measure of the food quality. Indicator strip 25 is similar to the embodiment illustrated in FIG. 2 with a shield layer 26 surrounding an indicator layer 22 and a substrate 24. To use the indicator strip, a portion of shield layer 26 is removed to expose a portion of indicator layer 22 to vapors from the food. One method for removing the portion of the shield layer is to cut away a portion 27 of the strip as shown in FIG. 3B, thereby exposing an edge 28 of indicator layer 22. As volatile bases from the food contact the exposed edge of the indicator layer, the indicator compound 30 at that edge changes color, as illustrated in FIG. 3C. The color 32 diffuses through the indicator layer with increased exposure to the volatile bases, as depicted in FIG. 3D.

Quantitative or semiquantitative measurements can be made using this strip by measuring the distance that the color diffuses over a predetermined time period at a particular temperature. In one embodiment, the food quality indicator device includes markings spaced at intervals to provide a convenient way for measuring the depth of the diffused color. Measurements of color diffusion can be compared to calibration samples to determine the quality of the food.

To obtain quantitative or semiquantitative measurements, the amount of indicator compound and the size of the exposed edge should be proportional to the weight of food in the container. Typically, samples of different types of food can not be compared, however, foods that are sufficiently similar (e.g., different types of fish) may yield comparable results, other factors being equal.

Figure 4:
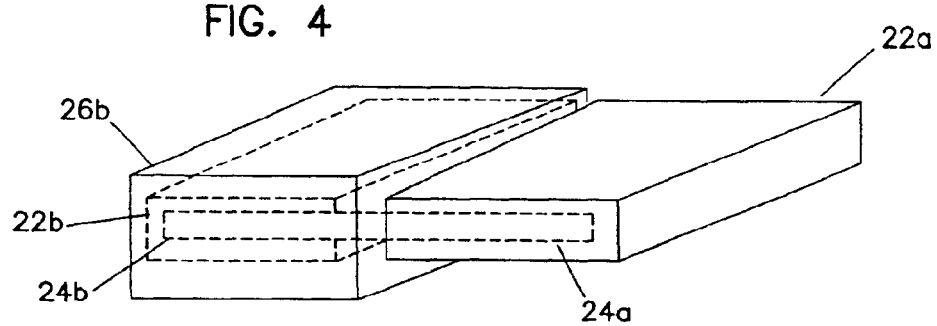
FIG. 4 is a side perspective view of a third embodiment of a food quality indicator device according to the present invention.

Another embodiment is illustrated in FIG. 4 in which two indicator layers 22a, 22b are disposed on one or more substrates 24a, 24b. Only indicator layer 22b is surrounded by an amine-impermeable shield layer 26b. Indicator layer 22a can be compared to layer 22b to determine when a color change has occurred due to the presence of volatile bases. Indicator layer 22b is prevented from changing color because of shield layer 26b. Comparison of the two indicator layers 22a, 22b provides a convenient method for determining when an indicator compound has changed color, especially when the color change is subtle or slight. Other configurations are possible.

Figure 5:
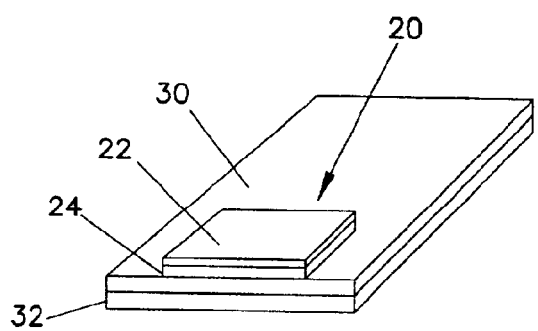
FIG. 5 is a side perspective view of the food quality indicator device of FIG. 1 mounted on a backing material according to the present invention.

FIG. 5 illustrates an embodiment of the invention in which indicator device 20 is provided on a backing material 30 that can be attached to food packaging. The attachment of backing material 30 to the packaging may be accomplished, for example, via an adhesive layer 32 applied to the backing material 30 or by bonding the backing material to the packaging using a curable resin or other bonding agent. Device 20 may also include an adhesive protection layer (not shown) manufactured with the device and taken off to expose the adhesive for application to packaging material or any other desired place. Device 20 is attached to backing material 30 by methods that include heat sealing or adhesive attachment. Device 20 may cover all or only a portion of backing material 30.

In another embodiment, device 20 is directly attached to food packaging via an adhesive or other method. In a further embodiment, indicator layer 20 is directly formed on food packaging material, using the packaging material as a substrate.

Figure 7:
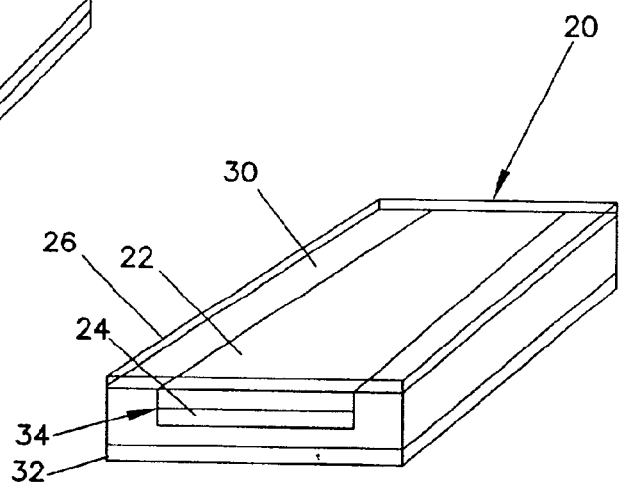
FIG. 7 is a side perspective view of the food quality indicator device of FIG. 2 mounted within a groove of a backing material according to the present invention.
Figure 6:
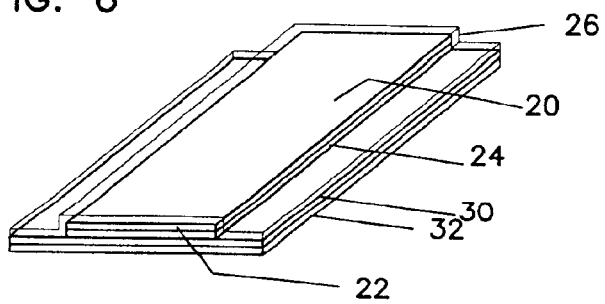
FIG. 6 is a side perspective view of the food quality indicator device of FIG. 2 mounted on a backing material according to the present invention.

FIGS. 6 and 7 illustrate two embodiments similar to that of FIG. 5 except that an amine-impermeable shield layer 26 is applied over indicator layer 22. The embodiment depicted in FIG. 6 shows an indicator device 20 on a backing material 30. A shield layer 26 is applied over device 20 and backing material 30 to prevent amine vapor from contacting the device except in a region from which the shield layer has been removed. Alternatively, device 20 may be constructed with a shield layer and then attached to backing material 30.

FIG. 7 shows a groove 34 into which device 20 is placed. An amine-impermeable shield layer 26 is then applied over device 20 and the raised portions of backing material 30 which define groove 34. Alternatively, shield layer 26 is formed over device 20 prior to placement of the device in groove 34.

The embodiments of FIGS. 6 and 7 may be manufactured with regions of device 20, such as an edge of the device, uncovered by shield layer 26. Alternatively, a portion of shield layer 26 may be removed (e.g., cut away) when the device is to be used.

Another embodiment of the invention includes two or more strips or strings, preferable positioned adjacent to each other. Each of the strips or strings contains a different formulation of the indicator compound and other additives to provide different sensitivities. For example, the formulation may differ by the amount of indicator compound or by the amount of acid added to the indicator compound. Typically, the two or more strips or strips are coated with a non-permeable coating.

In operation, the non-permeable coating is removed from an end of each of the strips or strings, as described above. A quantitative analysis of the contaminant can be determined by comparing the relative lengths of the strips or strings with altered color for a given period of time. These relative amounts, for example, can be compared to test samples for qualitatively or quantitatively determining the amount of contamination of the food.

Although at least some embodiments of the invention can be used to detect contamination in frozen food and at temperatures below 0° C., these same or other embodiments may be used to determine contamination at higher temperatures. For example, a bag containing a food sample and an indicator device may be heated, for example, boiled in water, to increase the emission rate of contaminants from the sample. In any case, the indicator device operates without water mediation, for example, in a sealed bag. Heating the food and the indicator device may decrease the amount of time required for detection of contamination.

One embodiment of a method for forming a food quality indicator device is to dissolve an indicator compound in water, methanol, ethanol, propanol, acetone, ether, or other indicator solvating liquid to provide a 0.01 to 1.0 mg/mL solution. About 1–10 mL of 0.01–1.0 M high-volatility acid, such as hydrochloric acid, acetic acid, formic acid, or trifluoroacetic acid is added to 50 mL of the indicator solution. 0–10 grams of a polymeric resin capable of dissolving in the solvent, 0–10 grams of hydrated alumina, and 0–10 grams of a non-volatile acid, such as phosphoric acid, are optionally added to the indicator solution.

In a separate container, 1–50 grams of a tetraalkoxysilane and 1–50 grams of an alkyl trialkoxysilane are mixed. The silane mixture is then added to the indicator/acid solution. This initiates the silane polymerization. At least a portion of the solution is then applied to the substrate before the silane polymerization is complete. The device is allowed to dry. Heating may be used to accelerate drying. Optionally, the device is then encased in a shield layer formed, for example, by polymerization of monomer materials around the layer or by application of one or more polymer films.

Although the invention has been exemplified with respect to the detection of volatile bases, such as amines, it will be understood that other volatile compounds, including, for example, volatile acids, such as $H_2S$ or mercaptans (i.e., thiols), can also be detected by the same or similar indicator devices. These volatile compounds, including volatile acids, may be generated, for example, by decomposition of food or by the presence of biological agents.

In particular, an indicator device can be formed using an indicator layer that changes color in the presence of a volatile acid. For example, an indicator compound may be used that produces a color change in a range from about pH 8 to about pH 14, preferably, in a range from about pH 9 to about pH 13, in aqueous solution. The indicator compound, should be capable of changing colors at temperatures below the freezing point of water and/or without mediation of water.

A polymeric matrix may be formed using, for example, a sol-gel glass formed by base catalyzed polymerization of alkoxysilanes. Preferably, the base is volatile. In addition, a non-volatile base may be disposed on the substrate of the indicator device to control the rate of response and/or detection sensitivity of the indicator device.

EXAMPLES

The following examples demonstrate methods for the manufacture and use of the food indicator strips of the invention. It is to be understood that these examples are merely illustrative and are in no way to be interpreted as limiting the scope of the invention.

Example 1

Preparation of a Food Quality Indicator Device Using Bromophenol Blue 50 mg of bromophenol blue were dissolved in 50 mL of ethanol. Five mL of 0.1 M HCl and five grams of polyvinyl alcohol (M.W. 2000) were added to the ethanol solution. Five grams of tetraethoxysilane and five grams of octadecyltriethoxysilane were mixed in a separate container. The silane mixture was then added to the ethanol solution with mechanical stirring. Paper strips and string were dipped into the solution and allowed to dry. After drying, the paper strips and string were coated with polyvinyl chloride (PVC) dissolved in tetrahydrofuran (THF). The THF was allowed to evaporate and the paper strips and strings were then laminated between two polypropylene films to form an amine-impermeable, transparent shield layer.

One edge of a strip and an end of a string were cut to expose the bromophenol blue indicator layer to a known spoiled cod sample at −20° C. for a period of one hour. Both the strip edge and the string end showed a dramatic color change from yellow to blue within the exposure period. The color change was also noticeable on a region of the strip and string adjacent to the open edge/end. This indicated that the volatile bases had diffused into the indicator device through the open edge/end.

Example 2

Preparation of a Food Quality Indicator Device Using Phloxine B a) Indicator strips and strings were made as described in Example 1 except that Phloxine B was used as the indicator and the PVC coating was not applied. In this case, the color change was from colorless or slightly pink to bright fuscia (i.e., pinkish red) after one hour exposure to the frozen spoiled cod sample.

b) Another set of indicator strips and strings was made. For this set, a hydrated alumina solution was made by stirring 10 grams of alumina in 50 mL of 1.0 M HCl for 15 hours at room temperature. 50 mg of Phloxine B was dissolved in 50 mL of ethanol and 5 mL of the hydrated alumina solution. Five grams of tetraethoxysilane and five grams of octadecyltriethoxysilane were mixed in a separate container. The silane mixture was then added to the ethanol solution with mechanical stirring. Paper strips and string were dipped into the solution and allowed to dry. After drying, the paper strips and string were laminated between two polypropylene films which formed an amine-impermeable, transparent shield layer.

One edge of a strip and an end of a string were cut to expose the Phloxine B indicator layer to a known spoiled cod sample at −20° C. for a period of one hour. Both the strip edge and the string end showed a dramatic color change from colorless or slightly pink to bright fuscia (i.e., pinkish red) within the exposure period. The color change also was noticeable on a region of the strip and string adjacent to the open edge/end. This indicated that the volatile bases had diffused into the indicator device through the open edge/end. However, the length of the color change was considerably shorter than for the Phloxine B strips and string described in a), possibly due to absorption of the volatile bases by the hydrated alumina in the indicator layer. This illustrates one way of controlling sensitivity of the food quality indicator device as the hydrated alumina may retard diffusion and reversibility of the color change.

Example 3

Preparation of Another Food Quality Indicator Device Using Phloxine B

Indicator strings were made. First, a hydrated alumina solution was made by stirring 10 grams of alumina in 50 mL of 1.0 M HCl for 15 hours at room temperature. In addition, two grams of polyacrylic acid were suspended in 100 mL of ethanol. 15 mg of Phloxine B and 0.285 mg of phosphoric acid were dissolved in 50 mL of ethanol, 5 mL of the hydrated alumina solution, and 5 mL of the polyacrylic acid suspension. Five grams of tetraethoxysilane and five grams of octadecyltriethoxysilane were mixed in a separate container. The silane mixture was then added to the ethanol solution with mechanical stirring. Polyester string was dipped into the solution and allowed to dry. After drying, the string was covered by Teflon™-spray (PTFE Release Agent Dry Lubricant MS122N/CO2 from MillerStevenson, Sylmar Calif.).

One edge of a strip and an end of a string were cut to expose the Phloxine B indicator layer to a known spoiled cod sample at −20° C. for a period of one hour. Both the strip edge and the string end showed a dramatic color change from colorless or slightly pink to bright fuscia (i.e., pinkish red) within the exposure period. The color change also was noticeable on a region of the strip and string adjacent to the open edge/end. This indicated that the volatile bases had diffused into the indicator device through the open edge/end.

Comparative Example

Exposure of Commercial pH Indicator Strips to a Spoiled Cod Sample at −20° C.

Commercial pH papers were exposed to the spoiled cod sample of Examples 1 and 2 at −20° C. for one hour just as the food quality indicator strips of Examples 1 and 2. The pH papers tested were a) ColorpHast™ pH 3.5–4.5 paper from EM-Reagents (Cat. No. 9581), b) pH Test Strips 0–14.0 from Sigma Chemical Company (Cat. No. P4786), and c) Alkacid Test Paper from Fisher Scientific Co. (Cat. No. 14839) with a range from pH 2 to 10. Paper a) showed a slight darkening in color, going from orange to orange-red, upon exposure to the sample, however the color reverted back to orange after 60 seconds at room temperature.

Similarly, paper b) showed a slight darkening of one color region, going from olive brown to a slightly darker hue, which reverted after 5 minutes at room temperature. There was no observed change in the color of pH paper c).

In contrast, the food quality indicator devices of Examples 1 and 2 had dramatic color changes, blue to yellow for the Bromophenol Blue indicator device and colorless or slightly pink to bright fuscia for the Phloxine B indicator device. In each case, the color change was permanent or lasted at least several weeks at room temperature after removal from the amine-containing environment.

The present invention should not be considered limited to the particular examples or embodiments described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. An indicator device, comprising:
   a substrate;
   a first polymeric matrix coated on the substrate;
   a second polymeric matrix covering all of the first polymeric matrix except for an edge of the first polymeric matrix, the second polymeric matrix impermeable to volatile bases generated by decomposing food; and
   an indicator compound disposed within the first polymeric matrix, the indicator compound being colorimetrically responsive at temperatures below 0° C. to the volatile bases generated by food decomposition;
   wherein the first polymeric matrix is formed by an acid catalyzed polymerization of a monomer material comprising a tetraalkoxysilane, an alkyl trialkoxysilane, or a mixture thereof;
   wherein a distance of colorimetric response of the indicator compound disposed within the first polymeric matrix increases with increased exposure to the volatile bases, wherein food quality can be determined by measuring the distance of colorimetric response over a predetermined time period at a particular temperature.

2. The device of claim 1, wherein the indicator compound comprises a compound with a color transition in a range from about pH 1.0 and about pH 6.0.

3. The device of claim 2, wherein the indicator compound comprises a compound with a color transition in a range from about pH 2.5 and about pH 5.0.

4. The device of claim 1, wherein the indicator compound comprises a compound with one or more acidic functional groups in the absence of amino or alkylamino functional groups, wherein at least one of the one or more acidic functional groups is —COOH, —$SO_3$, —$S(O_2)O$—, or salts thereof.

5. The device of claim 1, wherein the indicator compound is a halogenated xanthene dye, a sulfonated azo dye, or a sulfonated hydroxy-functional triphenylinethane dye.

6. The device of claims 5, wherein the indicator compound is Bromophenol Blue, Phloxine B, Rose Bengal, Congo Red, or Metanil Yellow.

7. The device of claim 1, wherein the device further comprises a polymeric resin disposed within the first polymeric matrix.

8. The device of claim 1, wherein the device further comprises an acidic material disposed within the first polymeric matrix.

9. The device of claim 8, wherein the acidic material is a hydrated alumina, a zeolite, or phosphoric acid.

10. The device of claim 1, wherein the device is adapted for inclusion in a food package.

11. The device of claim 1, wherein the substrate comprises paper, plastic, cotton, flax, resin, glass, fiber glass, or fabric.

12. The device of claim 1, wherein the device consists of materials suitable for use with food.

13. A food package for use with a food product, comprising:
   packaging for a food product; and
   an indicator device according to claim 1, associated with the packaging so as to be exposed to volatile bases emitted from the food product.

14. The food package of claim 13, comprising two or more indicator devices according to claim 1, each of the indicator devices having a different amount of indicator compound or having a different amount of acid provided with the indicator compound.

15. The food package of claim 13, adapted and configured for frozen red meat, pork, poultry, processed meat products, or seafood.

* * * * *